United States Patent

Maier et al.

[11] Patent Number: 5,910,239
[45] Date of Patent: Jun. 8, 1999

[54] POTENTIOMETRIC $CO_2$ SENSOR HAVING AN OPEN TITANATE- OR STANNATE-BASED REFERENCE ELECTRODE

[75] Inventors: Joachim Maier, Wiernsheim, Germany; Werner Sitte, Graz; Michael Holzinger, St. Veit an der Glan, both of Austria

[73] Assignee: Max-Plank-Gesellschaft Zur, Munich, Germany

[21] Appl. No.: 08/765,087

[22] PCT Filed: Jun. 29, 1995

[86] PCT No.: PCT/EP95/02525

§ 371 Date: Dec. 23, 1996

§ 102(e) Date: Dec. 23, 1996

[87] PCT Pub. No.: WO96/00895

PCT Pub. Date: Jan. 11, 1996

[30] Foreign Application Priority Data

Jun. 29, 1994 [DE] Germany ............................. 44 22 800

[51] Int. Cl.[6] .................................................. G01N 27/407
[52] U.S. Cl. ........................... 205/781; 204/424; 204/426; 204/435; 205/784; 205/786.5
[58] Field of Search ............................ 204/435, 421–429; 205/781, 784, 784.5, 786.5; 429/218

[56] References Cited

U.S. PATENT DOCUMENTS 4,505,804  3/1985  Mase et al. ............................. 204/425
4,715,944  12/1987  Yanagida et al. ....................... 204/426
5,454,923  10/1995  Nachlas et al. ......................... 204/427
5,545,468  8/1996  Koshiba et al. ......................... 429/218

FOREIGN PATENT DOCUMENTS 0060944  9/1982  European Pat. Off. .
0310206  4/1989  European Pat. Off. .
3905298  9/1989  Germany .
4112301  10/1992  Germany .
2167867  6/1986  United Kingdom .
2186091  8/1987  United Kingdom .

OTHER PUBLICATIONS

Science and Technology of Fast Ion Conductors, ed. by Harry L. Tuller and Minko Balkanski (Plenum Publishing Corp., 1989) Month Unavailable, Joachim Maier, pp. 299–301.

Electrical Sensing of Complex Gaseous Species by Making Use of Acid–Base Properties, J. Maier, Solid State Ionics 62 (1993) Month Unavailable pp. 105–111, North Holland.

Thermodynamic Investigations of $Na_2ZrO_3$ by Electrochemical Means Joachim Maier and Udo Warhus, J. Chem. Thermodynamics 1986, Month Unavailable, pp. 309–316, M–1884.

Primary Examiner—T. Tung
Attorney, Agent, or Firm—Fulbright & Jaworski, LLP.

[57] ABSTRACT

The invention relates to a a reference electrode for electrolytic cells, comprising a combination of (a) titanium dioxide and an alkali-metal or alkaline-earth-metal titanate or (b) tin dioxide and an alkali-metal or alkaline-earth-metal stannate as a homogeneous mixture.

25 Claims, 7 Drawing Sheets

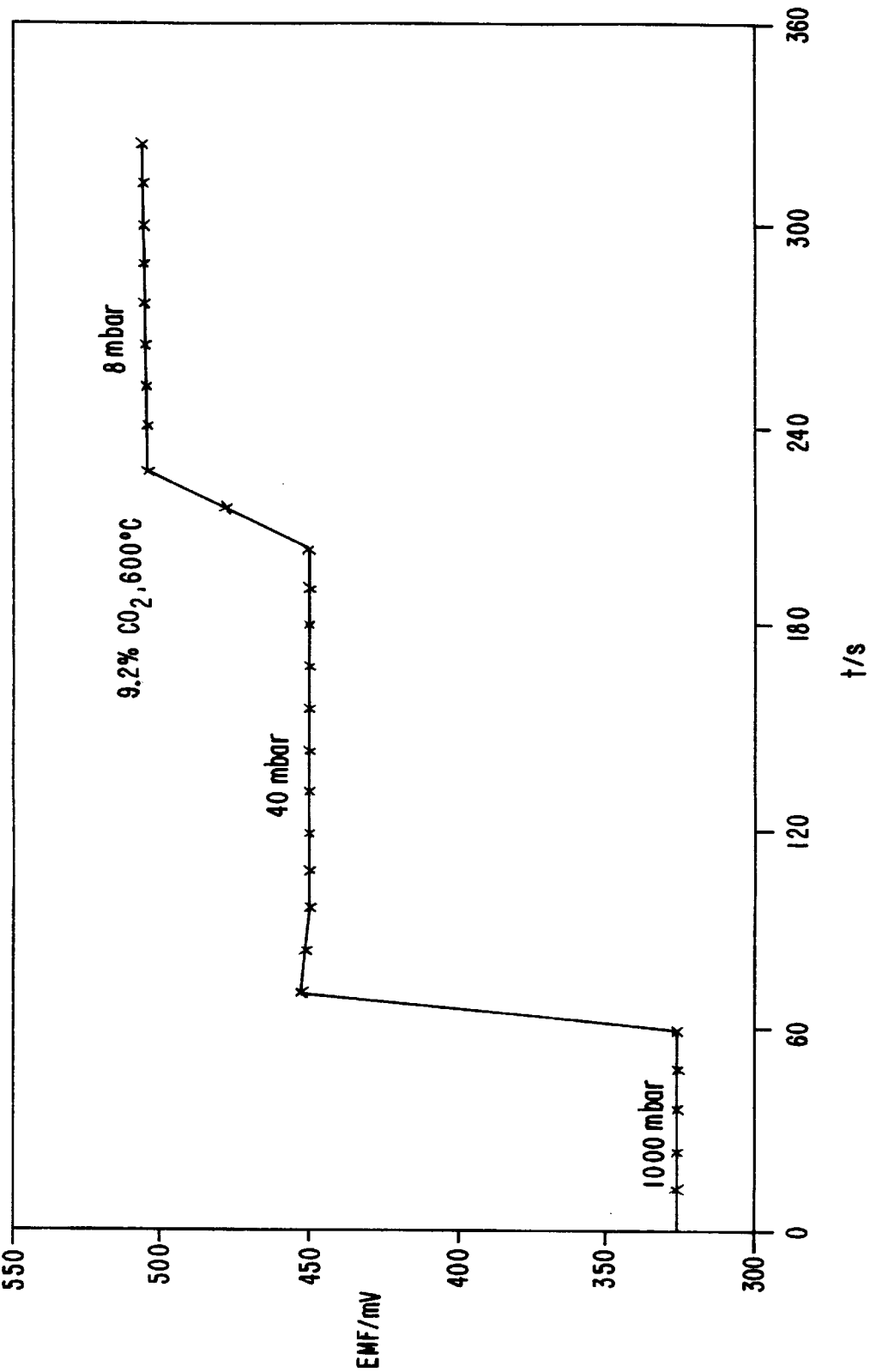
FIG. 7 Pt/CO2, Na2CO3/Na-β''-Al2O3/Na2Ti6O13,TiO2/Pt RESPONSE TO CHANGES IN CO2 PARTIAL PRESSURE, 600°C

POTENTIOMETRIC $CO_2$ SENSOR HAVING AN OPEN TITANATE- OR STANNATE-BASED REFERENCE ELECTRODE

BACKGROUND OF THE INVENTION

This invention relates to a titanate- or stannate-based reference electrode for electrolytic cells having an ion-conducting solid electrolyte, to sensors comprising the reference electrode of the invention and to use of the reference electrode for analyzing gases.

The use of electrolytic cells having a solid electrolyte as gas sensors, especially as oxygen sensors, has been known for a long time, However, it is difficult to realize reference electrodes of practical applicability. The use of cation-conducting solid electrolytes, for example a sodium-ion conductor, necessitates maintaining a defined sodium potential over long periods of time. According to prior art, this is achieved by making use of metallic sodium, which is liquid and highly reactive at the operating temperatures—frequently above 500° C.—of the sensor. The construction of such an electrode thus involves substantial difficulties, namely in insulating the electrode spaces hermetically from one another and from the surroundings. Reactions of the molten sodium with the insulating material or with other components of the electrolytic cell result in the stability of the sensor signal being impaired or in the sensor being totally destroyed with time.

In the DE-A-41 12 301.8 the alternative use of a reference electrode is suggested which contains an alkali-metal compound, in particular a sodium compound in multinary multi-phase equilibrium (e.g. binary Na/metal compounds or ternary Na/metal/oxide compounds). Examples of such reference electrodes having binary sodium/metal compounds are Na—Sb or Na—Bi, examples of such reference electrodes having ternary sodium/metal/oxide compounds are Na—Co-oxide or Na—Ni-oxide. However, on account of the toxicity of the heavy metal compounds used, production of these reference electrode systems is problematical.

It is also known that the metal activity brought about at the phase boundary between a solid electrolyte and a precious metal adhering thereto fulfills the function of a reference system (cf. Saito and Maruyama, Solid State Ionics 28–30 (1988), 1644). Here there is often the danger, however, that due to the inherently incomplete separation of reference and measuring electrodes the reference will react with the measuring medium, for example $CO_2$ and $O_2$. It is then only a matter of time until the cell voltage of a sensor of this type decreases to 0 and the reference electrode loses its functionality (cf. Maruyama et al., Solid State Ionics 23 (1987), 107).

Maier and Warhus (J. Chem. Thermodynamics 18 (1986), 309–316) describe thermodynamic studies carried out on $Na_2ZrO_3$ using electrochemical measurements. To this end an electrochemical cell was prepared which contained as reference electrode a mixture of sodium zirconate, zirconium dioxide and metallic gold. This reference electrode makes contact by way of a sodium-ion conductor with a measuring electrode containing a mixture of sodium carbonate and metallic gold. This electrochemical cell can also be used as a $CO_2$ sensor (cf. e.g. Maier, in: Science and Technology of Fast Ion Conductors, publ. H. L. Tuller and M. Balkanski, Plenum Press, New York (1989), pp. 299; Maier, Solid State Ionics 62 (1993, 105–111). This zirconate-based sensor has the advantage that the measuring electrode and the reference electrode in the cell can be exposed to the same $CO_2$ partial pressure, which means that the signal obtained depends only on the $CO_2$ and not on the $O_2$ partial pressure. It is therefore not necessary to seal the reference electrode.

BRIEF DESCRIPTION OF THE DRAWINGS

FIG. 7 shows the response of the titanate-based sensor of the invention to changes in the $CO_2$ partial pressure at 600° C.

Figure 1:
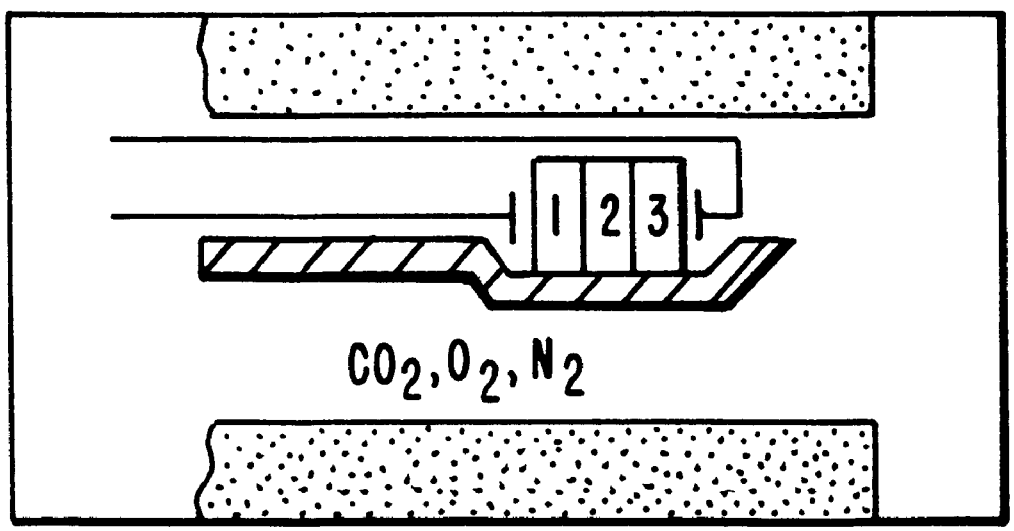
FIG. 1 shows the schematic assembly of a sensor according to the invention, having a reference electrode, a solid electrolyte and a measuring electrode.

One object of the present invention is to provide a reference electrode in which the disadvantages of the prior art are—at least in part—avoided. In particular, the reference electrode should be easy to make, should exhibit high long-term stability and should respond quickly to any change in the partial pressure of the gas to be measured.

This object is established according to the invention by provision of a reference electrode for electrolytic cells, comprising a combination of (a) titanium dioxide and an alkali- or alkaline-earth-metal titanate or (b) tin dioxide and an alkali- or alkaline-earth-metal stannate as a homogeneous mixture.

Surprisingly, it was found that a reference electrode comprising a combination of titanium dioxide ($TiO_2$) and an alkali- or alkaline-earth-metal titanate or of tin dioxide ($SnO_2$) and an alkali- or alkaline-earth-metal stannate responds markedly more quickly than do known reference electrodes to a change in the concentration of the gas to be measured. Furthermore, it is not necessary to seal off the reference electrode of the invention from the measuring medium; the reference electrode can be completely open, which means that considerable material and production problems can be avoided. The fact that this is possible is attributable to two criteria:

a) The oxygen itself determines the activity of the components on the reference side and therefore does not partake in the overall cell reaction. The EMF is no longer a function of the $O_2$ partial pressure.

b) The thermodynamic stability of the oxide mixtures is such that the reference side is also not sensitive to $CO_2$.

In addition, the reference electrode of the invention and an electrochemical sensor containing this reference electrode are thermodynamically fully defined, which means that reproducibility or drift problems are precluded.

The alkali-metal or alkaline-earth-metal titanate in the reference electrode of the invention preferably has the composition $X_mTi_nO_{2n+1}$, where X is an alkali-metal ion and m equals 2, or where X is an alkaline-earth-metal ion and m equals 1, and n is a natural number from 1 to 20, preferably from 1 to 12 and even more preferably from 3 to 8. A particularly preferred alkali-metal or alkaline-earth-metal titanate has the composition $X_mTi_6O_{13}$. A combination of $Na_2Ti_6O_{13}$ and $TiO_2$, for example, in a $CO_2$ sensor operating at a temperature of 500 to 600° C., has a response time within the range from $\leq 1$ to 2 seconds.

The alkali-metal or alkaline-earth-metal stannate in the reference electrode of the invention preferably has the composition $X_mSn_nO_{2n+1}$, where X is an alkali-metal ion and m equals 2, or where X is an alkaline-earth-metal ion and m equals 1, and n is a natural number from 1 to 20, preferably from 1 to 12 and even more preferably from 1 to 5. It is of particular advantage if the alkali-metal or alkaline-earth-metal stannate has the composition $X_mSnO_3$.

The titanate or stannate in the reference electrode can be an alkali-metal or alkaline-earth-metal titanate or stannate, preferably an alkali-metal titanate or stannate. Examples of suitable alkaline earth metals are beryllium, magnesium, calcium, strontium and barium. Examples of suitable alkali metals are lithium, sodium, potassium, rubidium and cesium, with lithium, sodium potassium and rubidium being preferred. Sodium is particularly preferred.

The most preferred titanate is $Na_2Ti_6O_{13}$, and the most preferred stannate is $Na_2SnO_3$.

The reference electrode of the invention preferably contains in addition a metallic substance which is homogenoeusly mixed with the other components, i.e. with the titanium or tin dioxide and the titanate or stannate. The metallic substance should be of such a nature that at the temperatures at which the reference electrode is used— preferably 300° to 800° C.—the substance is for the most part inert with respect to other solid and gaseous substances in the surroundings. For this reason it is preferable to select the metallic substance from the precious-metal group, e.g. gold, platinum, osmium, iridium, ruthenium, rhodium and palladium. It is especially preferable if gold or platinum are used as metallic substance.

The components of the reference electrode of the invention, i.e. the metal oxide, the titanate or stannate and, if use is made thereof, the metallic substance, form a homogeneous mixture. The reference electrode of the invention is preferably made by mixing together the powdered components and compressing the resulting mixture using known methods—isostatic pressing or cold-pressing, if necessary followed by sintering—so as to obtain a formed piece, e.g. a pellet.

The reference electrode of the invention contains the metal oxide, the titanate or stannate and, if use is made thereof, the metallic substance in proportions of preferably at least 1 vol. % of each, even more preferably at least 10 vol. % of each. It is of particular advantage if the reference electrode of the invention contains the individual components in approximately the same proportions by volume.

A further subject of the present invention is a sensor, in particular a sensor for measuring gases, having at least one reference electrode according to the invention and at least one measuring electrode suitable for the particular sensor function. The sensor preferably includes a reference electrode holder(s) for holding the reference electrode.

It is of advantage here if the reference electrode makes contact via an ion-conducting solid electrolyte with the measuring electrode. The ion-conducting solid electrolyte is preferably conductive for alkali-metal or alkaline-earth-metal ions, more particularly for whichever ion species is also contained in the reference electrode. It is thus of advantage if the solid electrolyte is an alkali-metal-ion conductor, e.g. a substance based on Nasicon, Lisicon or sodium beta aluminium oxide. It is of particular advantage if the solid electrolyte is a sodium-ion conductor. In addition, it is important that the ion conductor is for the most part inert at the operating temperature of the sensor.

The measuring electrode in the sensor according to the invention contains a compound which is in thermodynamic equilibrium with a gas to be measured. It is of advantage if this compound is an ionic compound with an alkali-metal or alkaline-earth-metal cation that is identical with the mobile cation of the solid electrolyte.

A measuring electrode for measuring $CO_2$, for example, can thus contain an alkali-metal or alkaline-earth-metal carbonate, for measuring $NO_x$ ($N_2O$, NO, $NO_2$) an alkali-metal or alkaline-earth-metal nitrate and for measuring $SO_x$ ($SO_2$, $SO_3$) an alkali-metal or alkaline-earth-metal sulfate.

It is of advantage if the sensor of the invention is a sensor for measuring $CO_2$, in which case the measuring electrode contains an alkali-metal or alkaline-earth-metal carbonate, preferably an alkali-metal carbonate and even more preferably sodium carbonate.

It is further of advantage if the measuring electrode contains a metallic substance which is mixed homogeneously with the other components. The metallic substance should be inert under the conditions at which the sensor operates, and it is preferably selected from the precious-metal group.

Besides the metallic substance and the compound in thermodynamic equilibrium with the gas to be measured, the measuring electrode can also contain different amounts of an ion-conducting solid electrolyte, preferably $\leq 10$ vol. %.

The principle according to which the sensor of the invention operates is that the alkali-metal or alkaline-earth-metal oxide activity on the reference side of the solid-electrolyte cell is kept constant by the phase mixture of titanium or tin dioxide/titanate or stannate, the component activity is determined by oxygen and not by the alkali- or alkaline-earth-metal itself, and the free chemical energy of the cell reaction:

$$n\ TiO_2 + Na_2CO_3 \rightleftharpoons CO_2 + Na_2(Ti_nO_{2n+1})$$

or $$n\ SnO_2 + Na_2CO_3 \rightleftharpoons CO_2 + Na_2(Sn_nO_{2n+1})$$

is negative, i.e. $CO_2$ does not react with $TiO_2$ or $SnO_2$. The $Na_2O$ activity on the measuring-electrode side of the cell varies by way of $Na_2CO_3$ as a function of the $CO_2$ partial pressure. As a consequence, the reference-electrode side of the cell can be exposed to the same $CO_2$ partial pressure as the measuring-electrode side, since the oxygen partial pressure is excluded from the overall balance. The measuring signal generated by the sensor of the invention is thus dependent exclusively on the partial pressure of the gas to be measured (e.g. $CO_2$) and not on the partial pressure of the oxygen in the measuring medium, which means that it is not necessary to insulate the reference electrode from the measuring medium. In addition, the sensor of the invention is fully defined thermodynamically.

A further subject of the this invention is the use of the reference electrode of the invention in a sensor, in particular for the measurement of gases, and the use of said sensor for the measurement of gases in order to obtain a signal which is independent of the partial pressure of the oxygen in the measuring medium. The sensor is used preferably for measuring $CO_2$, $NO_x$ or $SO_x$, most preferably for measuring $CO_2$.

EXAMPLE

1. Preparation of the Sensors

The following electrolytic cells having a solid electrolyte were prepared:

$Pt/CO_2$, $Na_2CO_3/Na$-$\beta''$-$Al_2O_3/Na_2SnO_3$, $SnO_2/Pt$ and
$Pt/CO_2$, $Na_2CO_3/Na$-$\beta''$-$Al_2O_3/Na_2Ti_6O_{13}$, $TiO_2/Pt$.

These cells were prepared by joining three pellets (1 cm in diameter, 1 cm thick). The solid-electrolyte pellet was made by isostatic pressing of Na-$\beta''$-aluminium oxide powder at 700 MPa. The measuring-electrode pellet was made by mixing refined platinum powder and powdered $Na_2CO_3$ (proportion by vol. 0.5), cold-pressing the mixture (400 MPa) and then sintering it. The reference electrode was made by mixing powdered platinum, $Na_2SnO_3$ and $SnO_2$ or $Na_2Ti_6O_{13}$ and $TiO_2$ in approximately equal volumes, cold-pressing the mixture (400 MPa) and then sintering it. Care was taken during preparation to avoid contact with moisture.

The assembly of the solid-electrolyte cell made up of these pellets is shown in FIG. 1. The sensor, consisting of measuring electrode (1), solid electrolyte (2) and reference electrode (3) is exposed directly to the measuring medium. For a given temperature the cell voltage is a function of the $CO_2$ partial pressure.

2. Carrying Out the Measurements

The cell potential of the sensors was recorded using a Keithley electrometer ($10^{14}$ Ω). The temperature was measured with a Pt/Pt+Rh thermocouple.

Figure 2:
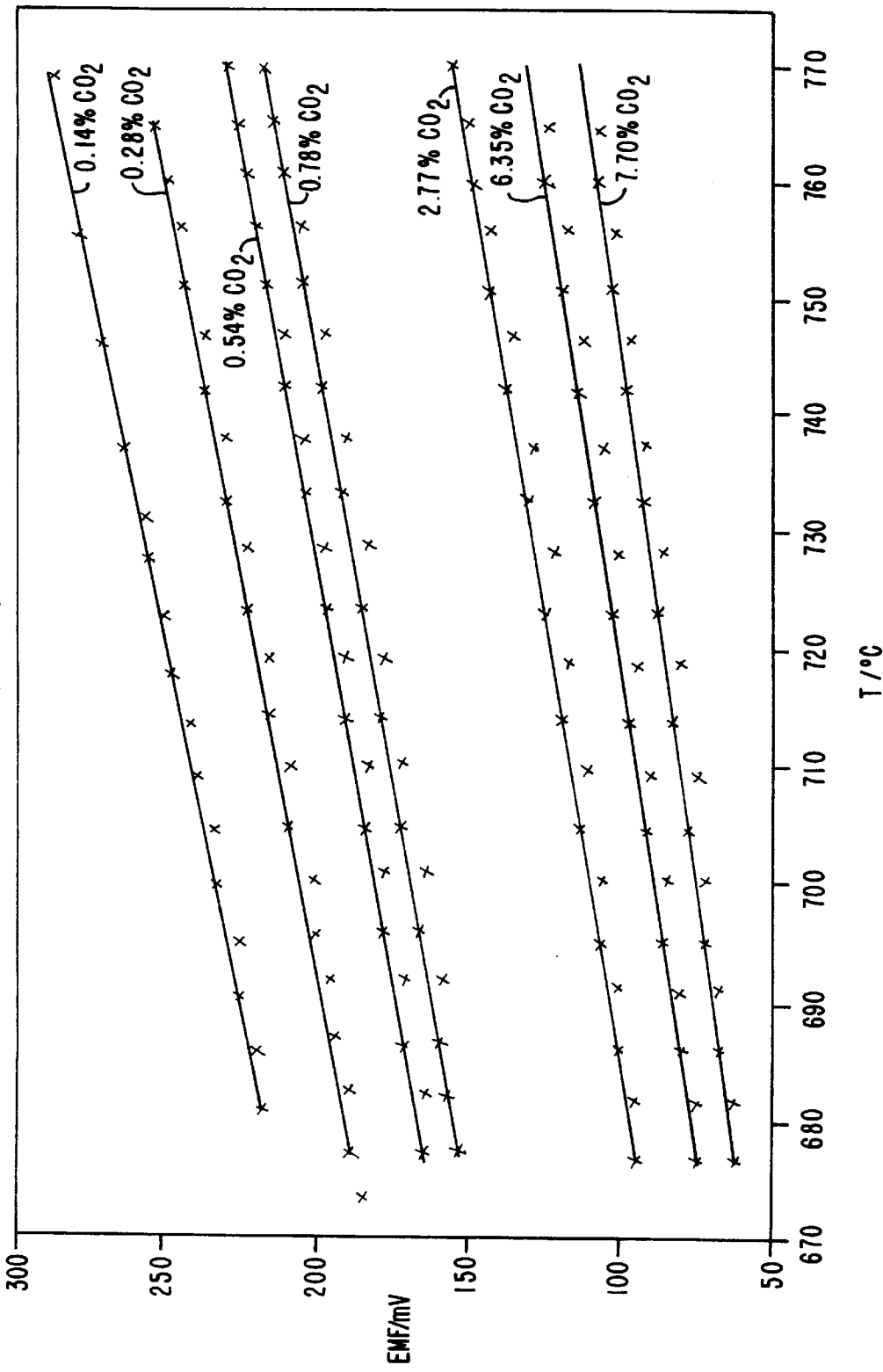
FIG. 2 shows the temperature dependence of the measuring signal generated by a stannate-based sensor of the invention in the range from 680 to 780° C. at various different $CO_2$ concentrations.
Figure 3:
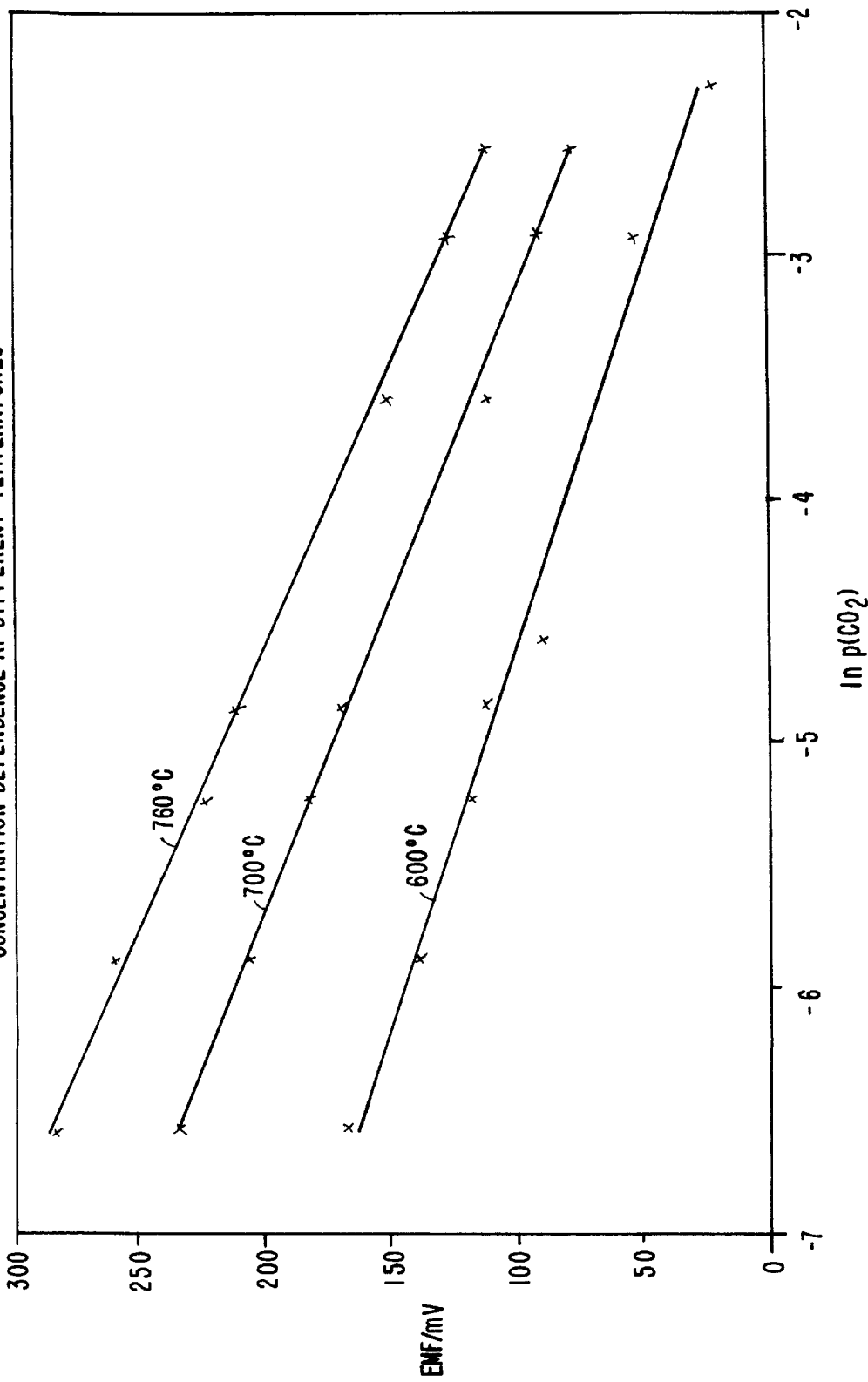
FIG. 3 shows the dependence of the measuring signal generated by a stannate-based sensor of the invention on the $CO_2$ partial pressure.

FIG. 2 shows the temperature dependence of the cell voltage (EMF) of the stannate-based sensor in the range from 680 to 780° C. at $CO_2$ concentrations from 0.14 to 7.70%. FIG. 3 shows the dependence of the measuring signal generated by this sensor on the $CO_2$ partial pressure at measuring temperatures of 600° C., 700° C. and 760° C.

Figure 4:
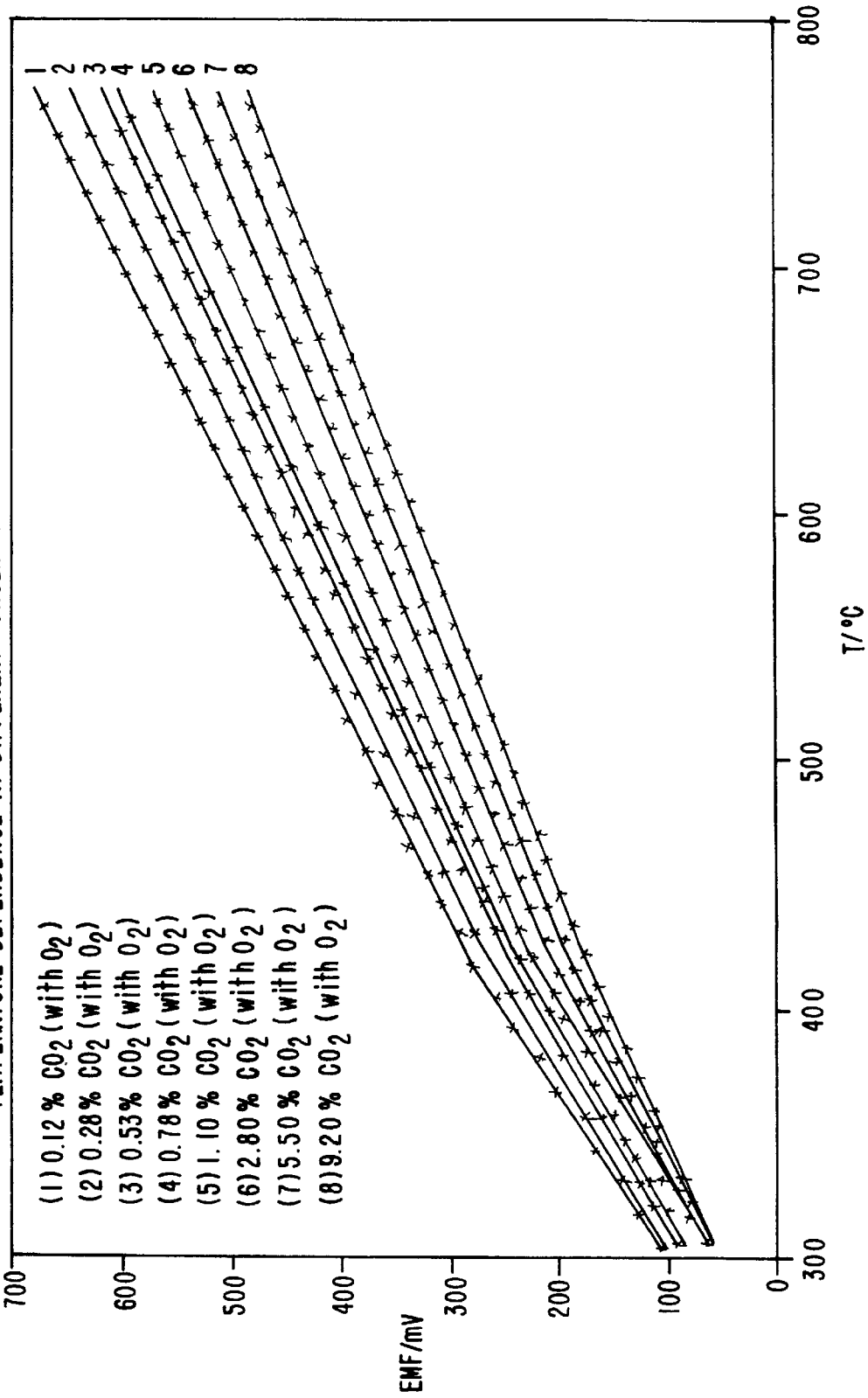
FIG. 4 shows the temperature dependence of the measuring signal generated by a titanate-based sensor of the invention in the range from 680 to 780° C. at various different $CO_2$ concentrations.
Figure 5:
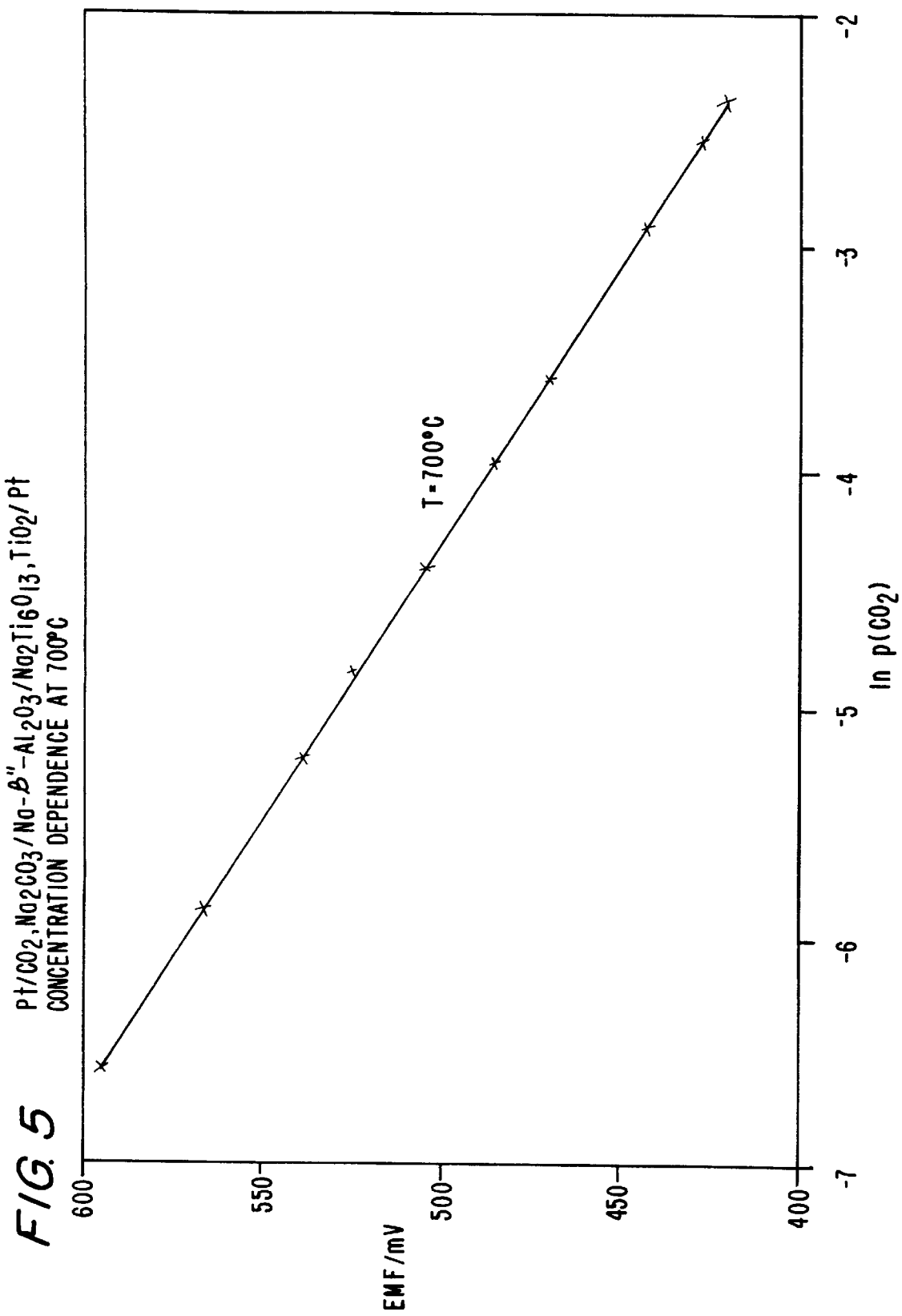
FIG. 5 shows the dependence of the measuring signal generated by a titanate-based sensor of the invention on the $CO_2$ partial pressure.

FIG. 4 shows the temperature dependence of the cell voltage of the titanate-based sensor at $CO_2$ concentrations from 0.12 to 9.20% $CO_2$. FIG. 5 shows the dependence of the measuring signal generated by this sensor on the $CO_2$ concentrations at 700° C.

Figure 6:
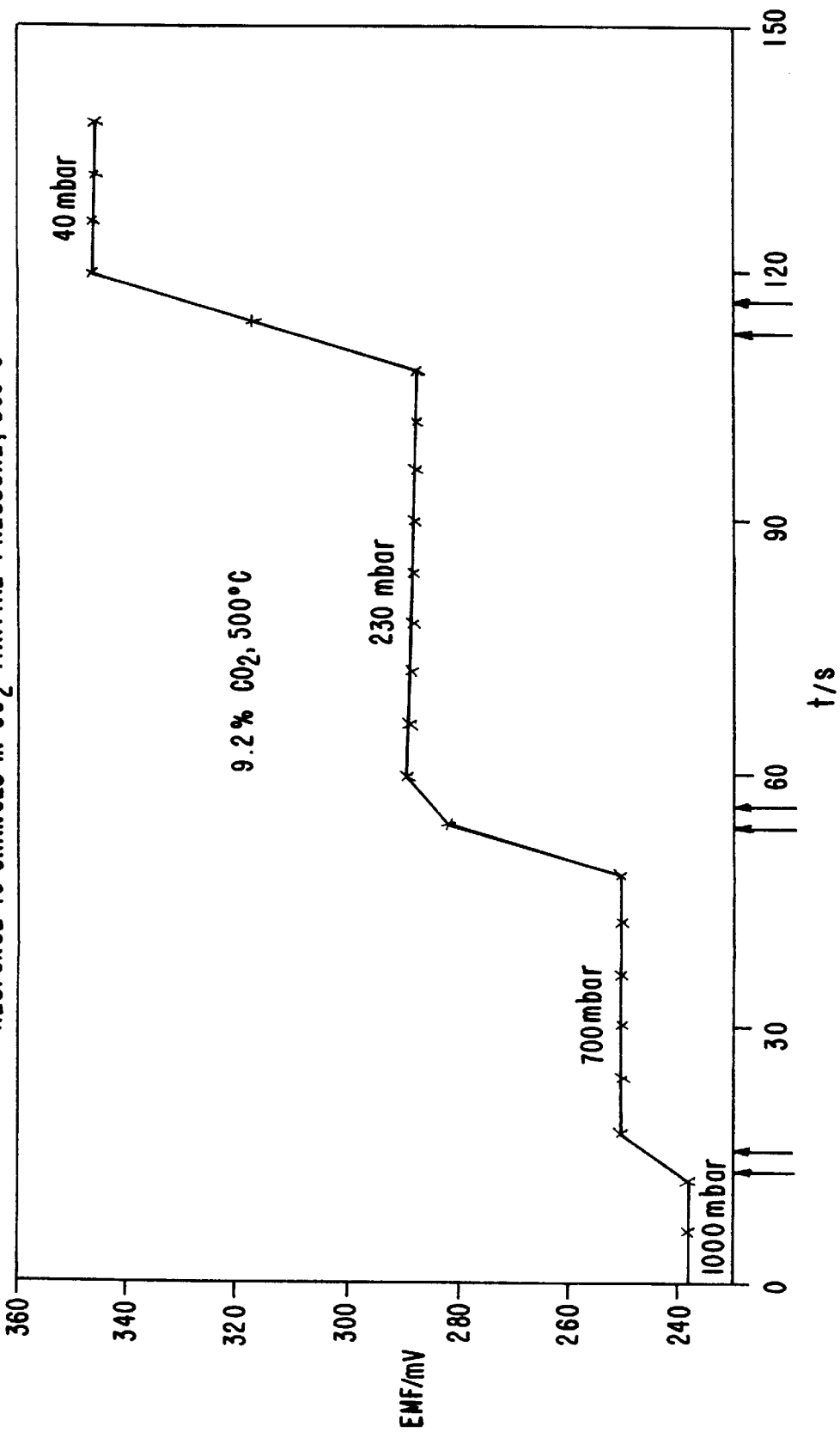
FIG. 6 shows the response of the titanate-based sensor of the invention to changes in the $CO_2$ partial pressure at 500° C.

FIGS. 6 and 7 show the response of the stannate-based sensor to changes in the $CO_2$ partial pressure at 500° C. and 600° C. respectively. Measurements were taken in each case at intervals of 10 seconds. Later measurements at shorter time intervals showed that the sensor responded within a time ≦2 seconds.

It will be understood that the specification and examples are illustrative but not limitative of the present invention and that other embodiments within the spirit and scope of the inventions will suggest themselves to those skilled in the art.

We claim:

1. A galvanic cell for measuring a gas comprising:
   (a) a reference electrode comprising a combination of (i) titanium dioxide and an alkali-metal or alkaline-earth-metal titanate or (ii) tin dioxide and an alkali-metal or alkaline-earth-metal stannate in intimate mixture, said reference electrode not being isolated from a gas medium to be measured;
   (b) a measuring electrode containing a compound which is in thermodynamic equilibrium with the gas to be measured; and
   (c) an ion-conducting solid electrolyte contacting the reference electrode and with the measuring electrode.

2. The galvanic cell of claim 1 wherein the alkali-metal or alkaline-earth-metal titanate of the reference electrode has the composition $X_m Ti_n O_{2n+1}$, where X is an alkali-metal ion and m equals 2 or X is an alkaline-earth-metal ion and m equals 1, and n is a natural number from 1 to 20.

3. The galvanic cell of claim 2 wherein the alkali-metal or alkaline-earth-metal titanate has the composition $X_m Ti_6 O_{13}$.

4. The galvanic cell of claim 1 wherein the alkali-metal or alkaline-earth-metal stannate of the reference electrode has the composition $X_m Sn_n O_{2n+1}$, where X is an alkali-metal ion and m equals 2 or X is an alkaline-earth-metal ion and m equals 1, and n is a natural number from 1 to 20.

5. The galvanic cell of claim 4 wherein the alkali-metal or alkaline-earth-metal stannate has the composition $X_m SnO_3$.

6. The galvanic cell of claim 1 wherein the titanate or stannate is an alkali-metal titanate or stannate.

7. The galvanic cell of claim 1 wherein titanate or stannate is sodium titanate or stannate.

8. The galvanic cell of claim 7 wherein the titanate is $Na_2Ti_6O_{13}$.

9. The galvanic cell of claim 7 wherein the stannate is $Na_2SnO_3$.

10. The galvanic cell of claim 1 wherein the reference electrode further comprises a metallic substance which is intimately mixed with said combination of (i) or (ii).

11. The galvanic cell of claim 10 wherein the metallic substance is a precious metal.

12. The galvanic cell of claim 1 wherein the reference electrode comprises titanium dioxide and the titanate, or tin dioxide and the stannate in proportions of at least 10 vol. % of each.

13. The galvanic cell of claim 12 wherein the reference electrode comprises said titanium dioxide and the titanate, or tin dioxide and the stannate in approximately equal proportions by volume.

14. The galvanic cell of claim 1 wherein the reference electrode is in the form of a press-formed piece.

15. A gas sensor comprising a galvanic cell according to claim 1 and a reference electrode holder.

16. The sensor of claim 15 wherein the ion-conducting solid electrolyte is conductive for alkali-metal or alkaline-earth-metal ions.

17. The sensor of claim 16 wherein the solid electrolyte is a sodium-ion conductor.

18. The sensor of claim 17 wherein the measuring electrode (b) contains (i) an alkali-metal or alkaline-earth-metal carbonate, (ii) an alkali-metal or alkaline-earth-metal nitrate, or (iii) an alkali-metal or alkaline-earth-metal sulfate.

19. The sensor of claim 18 for measuring $CO_2$ wherein the measuring electrode contains an alkali-metal or alkaline-earth-metal carbonate.

20. The sensor of claim 19 wherein the measuring electrode contains sodium carbonate.

21. The sensor of claim 17 wherein the measuring electrode further comprises a metallic substance which is mixed intimately with said compound which is in thermodynamic equilibrium with the gas to be measured.

22. The sensor of claim 21 wherein the metallic substance is a precious metal.

23. A method for measuring a gas in order to provide a signal which is independent of the partial pressure of the oxygen in a gas medium to be measured comprising contacting the sensor of claim 1 with a gas to be measured.

24. The method of claim 23 wherein the gas to be measured is selected from the group consisting of $CO_2$, $NO_x$, and $SO_x$.

25. The method of claim 23 wherein the gas to be measured is $CO_2$.

* * * * *